(12) United States Patent
Gonzalez et al.

(10) Patent No.: US 9,095,814 B2
(45) Date of Patent: *Aug. 4, 2015

(54) PROCESS FOR MEMBRANE SEPARATION OF AN OLEFIN THAT IS CONTAINED IN A HYDROCARBON MIXTURE

(75) Inventors: Serge Gonzalez, Decines (FR); Jacques Vallet, Lyons (FR); Arnaud Baudot, Vernaison (FR); Helene Rodeschini, Lyons (FR); Jean Pierre Reyt, Villette De Vienne (FR)

(73) Assignee: IFP ENERGIES NOUVELLES, Rueil Malmaison Cedex (FR)

( * ) Notice: Subject to any disclaimer, the term of this patent is extended or adjusted under 35 U.S.C. 154(b) by 1502 days.

This patent is subject to a terminal disclaimer.

(21) Appl. No.: 12/376,642

(22) PCT Filed: Jul. 6, 2007

(86) PCT No.: PCT/FR2007/001172
§ 371 (c)(1),
(2), (4) Date: Feb. 16, 2011

(87) PCT Pub. No.: WO2008/017743
PCT Pub. Date: Feb. 14, 2008

(65) Prior Publication Data
US 2011/0130611 A1    Jun. 2, 2011

(30) Foreign Application Priority Data

Aug. 9, 2006 (FR) ...................................... 06 07278

(51) Int. Cl.
| | | |
|---|---|---|
| *C07C 7/144* | (2006.01) | |
| *B01D 53/22* | (2006.01) | |
| *B01D 67/00* | (2006.01) | |
| *B01D 71/64* | (2006.01) | |

(52) U.S. Cl.
CPC .......... *B01D 53/228* (2013.01); *B01D 67/0018* (2013.01); *B01D 71/64* (2013.01); *C07C 7/144* (2013.01); *B01D 2323/06* (2013.01); *B01D 2323/08* (2013.01)

(58) Field of Classification Search
None
See application file for complete search history.

(56) References Cited

U.S. PATENT DOCUMENTS

| | | | |
|---|---|---|---|
| 4,968,331 A | | 11/1990 | Sakashita et al. |
| 5,215,554 A | * | 6/1993 | Kramer et al. ................... 95/47 |
| 5,409,525 A | * | 4/1995 | Kazama et al. ................... 96/14 |
| 5,837,032 A | * | 11/1998 | Moll et al. ........................ 95/45 |
| 5,964,925 A | * | 10/1999 | Ozcayir et al. ................... 96/14 |
| 6,180,008 B1 | * | 1/2001 | White ....................... 210/500.39 |
| 6,531,569 B1 | * | 3/2003 | Tachiki et al. ................ 528/289 |
| 6,790,263 B1 | * | 9/2004 | Ding et al. ........................ 96/13 |
| 2003/0233934 A1 | * | 12/2003 | Wijmans et al. .................. 95/46 |

FOREIGN PATENT DOCUMENTS

| | | |
|---|---|---|
| DE | 150 316 A3 | 8/1981 |
| EP | 0 412 881 A1 | 2/1991 |
| JP | 1-194905 A | 8/1989 |

OTHER PUBLICATIONS

Ilinitch, O. M., A. A. Lapkin, and K. I. Zamaraev. "Propylene in polyphenylene oxides membranes: unusual permeability vs. pressure behaviour." Journal of membrane science 98.3 (1995): 287-290.*
F. Piroux et al., "Gas Transport Mechanism in Sulfonated Polyimides Consequences on Gas Selectivity", Journal of Membrane Science, vol. 209 (2002) pp. 241-253.
S.I. Semenova, "Polymer Membranes for Hydrocarbon Separation and Removal", Journal of Membrane Science, vol. 231 (2004) pp. 189-207.
K. Tanaka et al., "Permeation and Separation Properties of Polyimide Membranes to Olefins and Paraffins", Journal of Membrane Science, vol. 121 (1996) pp. 197-207.

* cited by examiner

*Primary Examiner* — Krishnan S Menon
(74) *Attorney, Agent, or Firm* — Millen, White, Zelano & Branigan, P.C.

(57) ABSTRACT

This invention relates to the field of processes for membrane separation and applies in particular to the purification of C2 or C3 olefins. This process makes it possible more particularly to separate propylene from a mixture that contains other C3 hydrocarbons such as propane. The membranes that are used in the process according to this invention are vitreous polymer-based membranes whose pattern contains a bis-phenyl-9,9-fluorene group.

9 Claims, No Drawings

PROCESS FOR MEMBRANE SEPARATION OF AN OLEFIN THAT IS CONTAINED IN A HYDROCARBON MIXTURE

FIELD OF THE INVENTION

This invention belongs to the field of processes for membrane separation and applies to the purification of C2 or C3 olefins.

This process makes it possible more particularly to separate the propylene from a mixture that contains other C3 hydrocarbons, such as propane.

The membranes that are used in the process according to this invention are membranes based on amorphous, vitreous polymer or can have a very low crystallinity and whose pattern contains a bis-phenyl-9,9-fluorene group.

The membranes that are used in the process according to this invention have permeability/selectivity values that are higher than all of the values that are published in the prior art. In addition, the polymer membranes that are used in this invention retain very good separation properties under operating conditions that are close to those that are used in the industry, in particular those that involve high values of hydrocarbon partial pressure, known for being favorable to a deterioration in performance levels of most of the polymer membranes.

In a preferred version of the invention, the polymer that constitutes the selective layer of the membrane is of the polyimide type.

More particularly, the process according to this invention can be applied to the separation of C2 or C3 olefins that are contained in a mixture of hydrocarbon compounds that belong to other chemical families such as the paraffins.

EXAMINATION OF THE PRIOR ART

In the documents of the prior art, the separation performance levels of the membranes are generally described by means of two parameters: permeability and selectivity.

Permeability is defined as the flow density of material that passes through the membrane, added to the thickness of said membrane and to the partial pressure difference of the compounds that pass through the membrane applied between the upstream and downstream faces.

The selectivity of the membrane for the component A relative to the component B is defined as the ratio of the permeabilities of the two components A to B.

The permeability is measured in barriers (1 barrer=$10^{-10}$ $cm^3 \cdot cm/cm^2 \cdot cm_{Hg} \cdot s$, or in SI unit 0.75 $10^{-15}$ $Nm^3 \cdot m/m^2 \cdot s \cdot Pa$).

In the case of the separation of a binary mixture, the separation factor can be calculated in two ways: either from permeabilities that are obtained in pure objects (ideal selectivity or permselectivity is then the term used) or from data on the flows in a mixture (mixture selectivity or separation factor is then the term used).

The separation process that is described in this invention is carried out by a solution/diffusion mechanism through a dense polymer film that forms the selective layer of the membrane.

In general, the membranes that offer a high level of selectivity are not very permeable, and conversely, a very permeable membrane generally has selectivity values that are quite low.

Numerous polymer materials that are used in membrane form have been studied in the literature, in particular for the separation of olefins that are contained in an olefin/paraffin mixture.

The aromatic polyimides have been described for use in the separation of various gases. Certain aromatic polyimide membranes have then been developed for the purpose of providing relatively high selectivities, but the permeabilities still remain too low for an industrial application. Numerous studies in this field have focused on the use of polyimide membranes based on 4,4'-(hexafluoroisopropylidene)diphthalic anhydride (6FDA) because this compound imparts very good film-forming properties to the polymer material.

The prior art in the field of membrane separations that are applied to hydrocarbon mixtures is quite vast, and we will deal with the closest prior art represented by the patent U.S. Pat. No. 5,749,943 that describes the use of a homogeneous or symmetrical polyimide membrane based on 2,2-bis(4-aminophenyl)hexafluoropropane dianhydride 6FDA and diamine (FpDA) for the separation of unsaturated hydrocarbon from a mixture that contains said unsaturated compounds and saturated compounds. High selectivity values have been obtained, greater than 30, but the permeabilities remain low, less than 1 barrer (1 barrer=$10^{-10}$ $cm^3 \cdot cm/cm^2 \cdot cm_{Hg} \cdot s$), and the measurements are taken at 25° C.

Tanaka et al. (K. Tanaka, A. Taguchi, J. Hao, H. Kita, K. Okamoto, *Journal of Membrane Science* 121 (1996) 197-207 and K. Okamoto, K. Noborio, J. Hao, K. Tanaka, H. Kita, *Journal of Membrane Science* 134 (1997) 171-179) studied prepared polyimide membranes based on 2,4,6-trimethyl-1,3-phenylenediamine dianhydride 6FDA and diamine (TrMPD). These two publications are extracted from a journal whose title can be translated into French by "Journal de la Science des Membranes." The other articles that are cited are also extracted from this same journal.

The separation performance levels of these membranes are relatively good. Their propylene permeability coefficient is 30 barriers, and the ideal separation factor between propylene and propane is 11 to 323 K and 2 bar (1 bar=$10^5$ pascal).

The permeability coefficients of olefins and paraffins and the selectivity coefficients in polymers are essentially dependent upon the partial pressure of penetrating gases. For example, Semenova (S. I. Semenova, *Journal of Membrane Science*, 231 (2004) 189-207) showed the dependence of the permeability of the 6FDA-TrMPD polyimide on the partial pressure of propane and propylene.

However, the high-pressure industrial operating conditions are well known for being favorable to the plasticization phenomenon of the membrane and can lead to a significant decline of the performance levels of the latter.

In addition, it is important to note that the majority of the published selectivity data have been obtained from measurements taken on objects that may or may not be pure for a mixture of saturated and unsaturated hydrocarbons. According to Tanaka et al. (K. Tanaka, A. Taguchi, J. Hao, H. Kita, K. Okamoto, *Journal of Membrane Science* 121 (1996) 197-207), the propylene permeability and the propylene/propane selectivity are respectively 27 barriers and 10, when the measurements are taken on pure objects, at 50° C. and under 0.2 MPa. When it is a matter of a mixture of these two hydrocarbons, the values respectively fall to 20 barriers and 6 in selectivity, under the same temperature and pressure conditions.

This is why selectivity values that are obtained in pure objects with potentially plasticizing compounds cannot be directly extrapolated into mixtures, because under the mixing conditions, the separation performance levels of dense polymer membranes are most often degraded.

Surprisingly enough, the separation properties of the polymer membranes that are described in this invention that were not predictable for the propane/propylene mixtures prove to be astonishingly good. In addition, the membranes that are used in this invention make it possible to work under a high hydrocarbon partial pressure without their performance levels being altered.

SUMMARY DESCRIPTION OF THE INVENTION

This invention belongs to the field of the processes for membrane separation and applies to the separation of a C2 or C3 olefin that is contained in a mixture of other hydrocarbon compounds with a number of carbon atoms that is close to that of the olefin to be separated. A close number of carbon atoms is defined as a carbon atom number that is identical to or different by one unit from that of the olefin that is to be separated.

For example, this process makes it possible to separate the propylene from a mixture that contains other C3 hydrocarbons such as propane.

The invention relies on the selective permeation of the olefin that is to be separated through a dense polymer film. The presence of a particular bis-phenyl-9,9-fluorene-type group in a rigid polymer that is put in the form of a dense film that constitutes the membrane leads to excellent separation properties, in particular in terms of the permeability of said film with regard to olefin, while keeping the olefin/paraffin selectivity at a high value.

The membranes that are used in the process according to this invention are membranes of the polymer type that are vitreous, amorphous, or have low crystallinity, comprising, in the repetition pattern, at least one bis-phenyl-9,9-fluorene group.

The film that constitutes the selective layer of the polymer membrane can undergo a post heat treatment at a temperature of more than 250° C. for at least one hour, intended to increase the selectivity of the polymer film.

The invention therefore consists of a process for membrane separation in which the selective layer of the polymer membrane consists of a dense polymer film whose chemical structure contains a bis-phenyl-9,9-fluorene group.

The selective layer of the polymer membrane that contains the bis-phenyl-9,9-fluorene group is selected from the group that consists of the polymers of the following families: the polyimides, the polyamides, the polycarbonates, the polysulfones, the poly(amide imides), the poly(ether sulfones), the polyesters, or the copolymers or mixtures of polymers of these families.

Preferably, the selective layer of the polymer membrane that contains the bis-phenyl-9,9-fluorene group belongs to the family of polyamides.

Also preferably, the selective layer of the polymer membrane that contains the bis-phenyl-9,9-fluorene group belongs to the family of polycarbonates.

Even more preferably, the selective layer of the polymer membrane that contains the bis-phenyl-9,9-fluorene group belongs to the family of polyimides.

DETAILED DESCRIPTION OF THE INVENTION

This invention belongs to the field of processes for membrane separation and applies to the separation of a C2 or C3 olefin (i.e., an olefin that comprises 2 or 3 carbon atoms) that is contained in a mixture of other hydrocarbon compounds with a number of carbon atoms that is close to that of the olefin that is to be separated.

For example, this process makes it possible to separate the propylene from a mixture that contains other C3 hydrocarbons such as propane.

The process relies on the selective permeation of the olefin that is to be separated through a dense polymer film. The presence of a particular bis-phenyl-9,9-fluorene-type group in a rigid polymer that is put into the form of dense film constitutes the membrane and leads to excellent separation properties, in particular in terms of permeability of said film in relation to the olefin, while maintaining a high olefin/paraffin selectivity.

The membranes that are used in the process according to this invention are membranes of the polymer type that are amorphous, vitreous, or have low crystallinity, comprising, in the repetition pattern, at least one bis-phenyl-9,9-fluorene group.

The invention therefore consists of a process for membrane separation in which the selective layer of the polymer membrane consists of a dense polymer film whose chemical structure contains a bis-phenyl-9,9-fluorene group.

The selective layer of the polymer membrane that contains the bis-phenyl-9,9-fluorene group is selected from the group that consists of the polymers of the following families: the polyimides, the polyamides, the polycarbonates, the polysulfones, the poly(amide imides), the poly(ether sulfones), the polyesters, or the copolymers or polymer mixtures of these families.

In a first variant of the invention, the selective layer of the polymer membrane that contains the bis-phenyl-9,9-fluorene group belongs to the family of polyimides.

In a second variant of the invention, the selective layer of the polymer membrane that contains the bis-phenyl-9,9-fluorene group belongs to the family of polyamides.

In a third variant of the invention, the selective layer of the polymer membrane that contains the bis-phenyl-9,9-fluorene group belongs to the family of polycarbonates.

In a fourth variant of the invention, the selective layer of the polymer membrane that contains the bis-phenyl-9,9-fluorene group belongs to the family of polysulfones.

In a fifth variant of the invention, the selective layer of the polymer membrane that contains the bis-phenyl-9,9-fluorene group belongs to the family of poly(amide imides).

In a sixth variant of the invention, the selective layer of the polymer membrane that contains the bis-phenyl-9,9-fluorene group belongs to the family of poly(ether sulfones).

In a seventh variant of the invention, the selective layer of the polymer membrane that contains the bis-phenyl-9,9-fluorene group belongs to the family of polyesters.

Very preferably, the selective layer of the polymer membrane that contains the bis-phenyl-9,9-fluorene group belongs to the family of polyimides.

The polymer that constitutes the selective layer of the membrane can be a homopolymer, a copolymer, or a mixture of polymers.

The membranes that are used in this invention, in addition to the presence of the vitreous polymer that comprises at least one bis-phenyl-9,9-fluorene group in the repetition pattern, can contain mineral and organic feedstocks and additives that are intended to bring about an improvement in the separation factor and/or to promote permeability.

By way of example, it is possible to cite the mineral feedstocks such as the inorganic salts, the zeolites, the clays, the mesoporous compounds, the native or post-treated silicas, the carbon blacks, the pyrolyzed polymers, the carbon nanotubes, and the dendrimers.

The membranes that are used in this invention, in addition to the vitreous polymer that comprises at least one bis-phenyl-9,9-fluorene group in the repetition pattern, can also contain cross-linking agents that allow an improvement in the separation factor and/or permeability.

The membranes that are used in this invention can also be treated chemically, thermally, or by radiation, thus making it possible to improve the separation factor and/or to promote permeability.

In the repetition pattern, the polymer that constitutes the selective layer of the membrane according to the invention comprises at least one bis-phenyl-9,9-fluorene group of the general chemical formula:

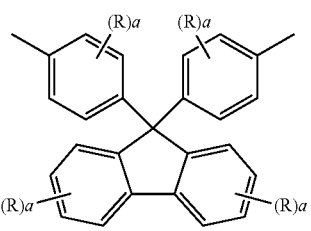

in which each of the groups R represents either a linear or branched alkyl group that has 1 to 16 carbon atoms, or a linear or branched alkoxy group that has 1 to 16 carbon atoms. For each of the groups R and independently from one group to the next, the index a can assume either the value of zero or a whole number between 1 and 4. Each value of the index a preferably will be 0 or 1.

Even more preferably, the index a will have a value of zero, which comes down to the elimination of the groups R.

For the alkyl groups, it is possible to cite in a nonlimiting manner the groups methyl, ethyl, propyl, isopropyl, and the linear or branched butyl groups.

For the alkoxy groups, it is possible to cite in a nonlimiting manner the groups methoxy, ethoxy, propyloxy, and the linear or branched butyloxy groups.

In a preferred version, the polymer that constitutes the selective layer of the membrane will be a homopolymer or a copolymer of general formula:

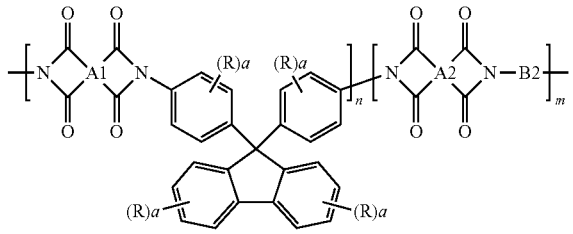

where A1 and A2 are hydrocarbon-containing tetravalent organic groups that are selected from among aromatic, alicyclic and aliphatic hydrocarbon groups, and the group B2 is a hydrocarbon-containing bivalent organic group that is selected from among the aromatic, alicyclic and aliphatic hydrocarbon groups. The indices m and n represent a positive whole number that corresponds to the degree of polymerization.

In a preferred version, the polyimide that constitutes the selective layer of the membrane is a statistical, alternate, sequenced or block polymer.

The method most generally used for obtaining the polyimide that constitutes the selective layer of the membrane results from the chemical reaction between:

a diamine that comprises in its structure the bis-phenyl-9, 9-fluorene group of general formula:

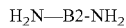

and a dianhydride of general formula:

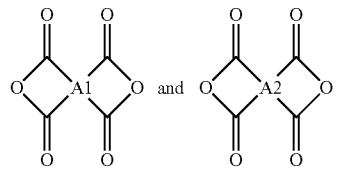

Within the scope of the invention, it will be possible to use a precursor, such as, for example, a tetra-carboxylic acid or the hemiester of a tetra-carboxylic acid.

Within the scope of the invention, the diamine can be selected from the following list:
1a 1,4-Diamino-2,3,5,6-tetramethylbenzene
bis(4-Aminophenyl)ether
2,4-Diamino-1-isopropylbenzene
The diaminoanthraquinones
2,7-Diaminofluorene
4,4'-Diamino-3,3'-dimethoxybiphenyl
2,4-Diaminotoluene
Diaminodiphenylsulfone
bis[4-(4-Aminophenoxy)phenyl]sulfone
9,10-bis(4-Aminophenyl)anthracene
1,4-bis(4-Aminophenyl)benzene
bis(4-Aminophenyl)methane
bis(4-Amino-3-ethylphenyl)methane
bis(4-Amino-3-methylphenyl)methane
bis(4-Amino-3-chloro-phenyl)methane
bis(4-Aminophenyl)sulfide
2,2-bis(4-Amino-3-hydroxyphenyl)propane
4,4'-Diamino-3,3'-dichlorobiphenyl
4,4'-Diamino-3,3'-dihydroxybiphenyl
4,4'-Diaminobiphenyl
9,9-bis(4-Aminophenyl)fluorene
bis(4-Amino-2,6-methylphenyl)methane
1,4-Diamino-2,5-dichlorobenzene
1,4-Diamino-2,5-dimethylbenzene
1,3-Diamino-2,4,6-trimethylbenzene
bis(3-Aminopropyl)tetramethyldisiloxane
2,5-Diaminopyridine
4,4'-Diaminobenzanilide
1,5-Diaminonaphthalene
1,3-Diamino-5-trifluoromethylbenzene
4,4'-Diamino-3,3',5,5'-tetramethylbiphenyl
3,3'-Diamino-4,4'-dihydroxybiphenyl
1,3-Phenylenediamine
1,4-Phenylenediamine
1,4-bis(4-Aminophenoxy)benzene.

Preferably, the diamines will be selected from the following list:
1a 1,4-Diamino-2,3,5,6-tetramethylbenzene
9,9-bis(4-Aminophenyl)fluorene
1,3-Diamino-2,4,6-trimethylbenzene
bis(3-Aminopropyl)tetramethyldisiloxane.

Within the scope of the invention, the dianhydride that is selected can be selected from the following list:
bis(3,4-Dicarboxyphenyl)sulfonic acid dianhydride
2,2-bis(3,4-Dicarboxyphenyl)hexafluoropropanoic acid dianhydride
1,1-bis(3,4-Dicarboxyphenyl)ethanoic acid dianhydride
Pyromellitic anhydride
2,3,6,7-Naphthalenetetracarboxylic acid dianhydride
3,3',4,4'-Biphenyltetracarboxylic acid dianhydride
1,2,5,6-Naphthalenetetracarboxylic acid dianhydride
2,2',3,3'-Biphenyltetracarboxylic acid dianhydride
3,3',4,4'-Benzophenonetetracarboxylic acid dianhydride
Oxydiphthalic acid dianhydride
1,4,5,8-Naphthalenetetracarboxylic acid dianhydride
2,2-bis(3,4-Dicarboxyphenyl)propanoic acid dianhydride
3,4,9,10-Perylenetetracarboxylic acid dianhydride
1,1-bis(2,3-Dicarboxyphenyl)ethanoic acid dianhydride
bis(2,3-Dicarboxyphenyl)methanoic acid dianhydride
bis(3,4-Dicarboxyphenyl)methanoic acid dianhydride.

The dianhydride will preferably be selected from the following list:

2,2-bis(3,4-Dicarboxyphenyl)hexafluoropropanoic acid dianhydride
Pyromellitic anhydride
3,3',4,4'-Biphenyltetracarboxylic acid dianhydride
3,3',4,4'-Benzophenonetetracarboxylic acid dianhydride.

The solvents that are necessary for the implementation of the polymerization can be selected from the following list:
N,N-Dimethylformamide
N,N-Diethylformamide
N,N'-Dimethylacetamide (DMAC)
N,N-Diethylacetamide
N-Methyl-2-pyrrolidone (NMP)
N-Cyclohexyl-2-pyrrolidone
Phenol
o-, m-, p-Cresol
Xylenol
Halogenated phenols
Catechol
Hexamethylphosphoramide
Dimethylpropyl urea
Benzyl alcohols
Lactates
Lactones such as γ-butyrolactone.

The solvents will preferably be selected from the following list:
N,N-Dimethylacetamide (DMAC)
N-Methyl-2-pyrrolidone (NMP)
o-, m-, p-Cresol
Lactones such as γ-butyrolactone.

These solvents can be used alone or in a mixture.

The knowledge of the molecular weight of the polymer is not essential, and it will be preferable to follow the evolution of the inherent viscosity of the polymer that should be at least greater than 0.1 dl/g and preferably between 0.3 dl/g and 2 dl/g. The inherent viscosity is defined relative to a reference viscosity and to the concentration of the polymer in solution in the solvent. Its value is homogeneous, unlike said concentration, i.e., 1 dl/g (=0.1 m$^3$/kg).

Most of the polymers that are being considered for implementation in membrane form in this invention are soluble in a large variety of organic solvents including most of the aprotic solvents, which are generally used for the formation of polymer membranes such as NMP.

The polymer membrane that contains the bis-phenyl-9,9-fluorene group can be homogeneous or asymmetrical.

In a variant of the process according to the invention, the polymer that constitutes the selective layer of the membrane will be a polyimide that is obtained from the polycondensation, on the one hand, of the 3,3',4,4'-biphenyltetracarboxylic acid dianhydride, and, on the other hand, a mixture of the 9,9-bis(4-aminophenyl)fluorene diamine and the 1,3-diamino-2,4,6-trimethylbenzene diamine.

In another variant of the process according to the invention, the polymer that constitutes the selective layer of the membrane is a polyimide that is obtained from the polycondensation, on the one hand, of the 3,3',4,4'-benzophenonetetracarboxylic acid dianhydride and, on the other hand, a mixture of the 9,9-bis(4-aminophenyl)fluorene diamine and the 1,3-diamino-2,4,6-trimethylbenzene diamine.

The polymer that constitutes the selective layer of the membrane can be used in the form of film or fibers according to the techniques that are known to one skilled in the art.

Once synthesized, the polymer in the form of a solid is dissolved in a suitable solvent such as NMP, for example, with a polymer content on the order of 1% to 50% by weight, and preferably between 5% and 20% by weight.

The solution is extended in film form with the desired thickness on a flat substrate or on a substrate that comes in the form of hollow fibers or else is extruded through a conventional spinner.

It is possible to produce the membrane, and composite membrane will then be the term used, by depositing a polymer film that comprises in its chain at least one bis-phenyl-9,9-fluorene group with a thickness of between 0.05 and 1 micron (1 μm=10$^{-6}$ meter) on a substrate that was previously used in the form of hollow fibers.

The substrate advantageously will be selected so that it offers the advantage of being much more permeable than the polyimides in general and does not contribute significantly to the resistance to the transfer of material through the resulting composite membrane.

According to an embodiment of the invention, the substrate will be a porous layer or a hollow fiber that consists of a polymer material such as, for example, a polysulfone, a polyethersulfone, a polyetherimide, a vinylidene polyfluoride, a polyethylene or a polypropylene, a polyacrylonitrile, a polyimide, a phenylene polyoxide, or a polymer derivative of cellulose, such as a cellulose acetate or an ethyl cellulose. The substrate can be a polymer that consists of different organic or mineral materials.

The adhesion between the selective layer and the substrate in some cases requires physical or chemical treatments that are well known to one skilled in the art.

Hereinafter, the separation of propylene contained in a mixture of propylene and propane will be taken as an example. It should be kept in mind, however, that this process applies as well to the separation of ethylene from a mixture that contains other C2 hydrocarbons.

The membranes of this invention can be used in various types of modules intended for the production of the separation unit. The final separation module can consist of one or more membranes. The module can be assembled with other identical modules so as to form a separation unit that has the desired size.

During operation, the mixture that contains the olefin that is to be separated is brought into contact with one of the sides of the membrane. By imposing a pressure difference between the side of the feedstock and the permeate side, the olefinic compounds pass through the membrane at a higher speed than the paraffins that comprise the same number of carbon atoms. Thus, a C3 olefin passes through the membrane more quickly than a C3 paraffin. This difference in speed produces a hydrocarbon stream that is enriched with olefin, which is sampled from the permeate side of the membrane.

This invention is not intended only for gas phase separations but can be extended to other types of separation, in liquid phase, for example, for temperature and pressure conditions that cover a broad field of use. In addition, the separation can take place for mixtures that contain more than two components.

Broadly speaking, the process for membrane separation according to the invention operates at a temperature of between −80 and 200° C. and at a pressure of between 0.1 MPa and 10 MPa. The pressure is defined as that of the mixture that is to be separated.

Most often, the process according to the invention operates at a temperature of between −60 and 100° C. and at a pressure of between 0.1 MPa and 5 MPa.

Preferably, the process according to the invention operates at a temperature of between 30° C. and 80° C. and at a pressure of between 0.1 MPa and 3 MPa. Also preferably, the process according to the invention operates at a temperature of between 40° C. and 70° C., and at a pressure of between 1 MPa and 2 MPa. Under the operating conditions of the process according to the invention, the partial pressure of olefin is generally more than 0.3 MPa.

EXAMPLES ACCORDING TO THE INVENTION

Example 1

According to the Invention

The polymer that is the object of Example 1 is the result of polycondensation of the hexafluoropropylidene-4,4'-diphthalic acid dianhydride (6FDA) and the 9,9-bis(4-aminophenyl)-fluorene (BDAF) in an equimolar mixture.

After purification of the monomers by recrystallization in suitable solvents, the polycondensation of the polyimide is carried out in two stages: in a first step, the acid polyamide is produced at ambient temperature, and then the polyimide is obtained in a second cyclization stage by a chemical method.

During the first polymerization stage, the mixing of the dianhydride and the diamine is carried out under inert atmosphere and in an anhydrous medium in the N,N-dimethylacetamide solvent (DMAC). The cyclo-dehydration stage is carried out by drop-by-drop addition of a cyclizing mixture that consists of triethylamine and acetic anhydride mixed in the synthesis solvent.

The thus obtained polyimide is then precipitated in water and then ground. The solid polymer is then filtered, rinsed, and then vacuum-dried in a furnace by gradually increasing the temperature until reaching 150° C. The inherent viscosity of the polymer that is thus obtained is 1.3 dl/g.

The material in ground form is then put into solution in the DMAC at a mass concentration of 12% under the action of vigorous mechanical stirring at ambient temperature.

The clear solution is then filtered under a pressure of 0.2 MPa on a Millipore-type filter that has a cutoff threshold of 1 μm. This solution is then put into the form of a film using a 300 μm spiraled bar on a glass plate that was previously degreased with acetone, and then dried.

The plate is inserted into a furnace. The evaporation of the solvent is carried out by a gradual elevation of the temperature up to 200° C. The final temperature is kept level for two hours. After cooling, the plate is immersed in water, where the separation of the film is observed.

After the solvent evaporates, the film that is obtained has a mean thickness of 20 μm.

A sample of this film was then tested in a circular permeation cell with an effective diameter of 5.5 cm placed in a thermostated chamber.

The upstream face of the thus tested membrane is flushed for 72 hours with a gas stream of 10 Nl/h that consists of propylene and propane, whereas the compartment downstream from the membrane, in which the permeate is collected, is flushed by a nitrogen stream of 1 Nl/h at atmospheric pressure.

The composition of the different fluids entering and exiting from the different compartments of the permeation cell is obtained by gas phase chromatography.

The sustained performance levels of the thus tested film are as follows:

TABLE 1

Performance Levels of the 6FDA-BDAF Polyimide Membrane (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 | 0.8 MPa | 50° C. | 84 Barrers | 7 |
| 70/30 | 0.8 MPa | 50° C. | 80 Barrers | 6.2 |

TABLE 2

Performance Levels of the 6FDA-BDAF Polyimide Membrane (Load Pressure = 1.7 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 | 0.8 MPa | 60° C. | 90 Barrers | 6.8 |
| 70/30 | 0.8 MPa | 60° C. | 85 Barrers | 6 |

Example 2

According to the Invention

The synthesis of the polyimide is carried out in two stages. During the first stage, the 6FDA-type dianhydride is put into contact with the BDAF in the N-methylpyrrolidone solvent (NMP) under inert atmosphere and in an anhydrous medium.

After 3 hours of stirring at ambient temperature, the acid polyamide is obtained.

The second stage consists of a thermal dehydration of this acid polyamide by heating (30 minutes at 100° C., 1 hour at 160° C., 1 hour at 180° C., and two hours at 200° C.).

The thus obtained polyimide is then precipitated in water, ground, and dried as described in Example 1 of this invention. The inherent viscosity of the thus obtained polymer was 0.55 dl/g.

The polymer is then dissolved again in the NMP solvent at a mass concentration of 10%. The clear solution is then filtered under a pressure of 0.2 MPa on a Millipore-type filter that has a cutoff threshold of 1 μm. This solution is then put into the form of a film using a 300 μm spiraled bar on a glass plate that was previously degreased with acetone, and then dried.

The plate is inserted into a furnace. The evaporation of the solvent is carried out by a gradual elevation of the temperature up to 200° C.

After the solvent evaporates, the film that is obtained has a mean thickness of 32 µm.

The performance levels of the film according to Example 2 for the propylene/propane separation have been obtained under test conditions that are identical to those described in Example 1.

TABLE 3

Performance Levels of the 6FDA-BDAF Polyimide Membrane (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 Mixture | 0.8 MPa | 50° C. | 3.0 Barrers | 12 |
| 70/30 Mixture | 0.8 MPa | 50° C. | 3.4 Barrers | 10 |

TABLE 4

Performance Levels of the 6FDA-BDAF Polyimide Membrane (Load Pressure = 1.7 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 | 0.8 MPa | 60° C. | 3.2 Barrers | 10 |
| 70/30 | 0.8 MPa | 60° C. | 3.0 Barrers | 8 |

Example 3

According to the Invention

The synthesis of the polyimide film is carried out according to the process that is described in Example 2. After the solvent evaporates, the film that is obtained has a mean thickness of 30 µm.

Once dried, the film is annealed in a study under nitrogen at 350° C. for 2 hours.

The performance levels of the film that is obtained according to Example 3 for the propylene/propane separation have been measured under test conditions that are identical to those described in Example 1.

TABLE 5

Performance Levels of the 6FDA-BDAF Polyimide Membrane According to Example 3 (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 Mixture | 0.8 MPa | 50° C. | 1.8 Barrers | 13 |
| 70/30 Mixture | 0.8 MPa | 50° C. | 1.3 Barrers | 12 |

If the performance levels of the membrane that is described in Example 2 (without post heat treatment) and the membrane that is described in Example 3 that is synthesized analogously but that has undergone a post heat treatment are compared, it is clear that the annealing of the membrane film leads to an increase in mixture selectivity.

Example 4

Example According to the Invention

The BTDA-BDAF polymer film that is the object of Example 4 is the result of the polycondensation of the 3,3',4,4'-benzophenonetetracarboxylic acid dianhydride (BTDA) and the 9,9-bis(4-aminophenyl)fluorene (BDAF) in an equimolar mixture.

After purification of the monomers by recrystallization in appropriate solvents, the polycondensation of the BTDA-BDAF polyimide is carried out in two stages: in a first step, the acid polyamide is produced, and then the polyimide is obtained in a second cyclization stage that is obtained by a chemical method.

During the first polymerization stage, the mixing of the dianhydride and the diamine is carried out under inert atmosphere and in an anhydrous medium in the NMP solvent.

The cyclo-dehydration stage is carried out by drop-by-drop addition of a cyclizing mixture that consists of triethylamine and acetic anhydride mixed in the synthesis solvent.

The thus obtained polyimide is then precipitated in water and then ground. It is then filtered, rinsed, and then vacuum-dried in a furnace by gradually increasing the temperature until reaching 150° C. The inherent viscosity of the thus obtained polymer is 0.8 dl/g in the NMP.

The material in ground form is then put into solution in the NMP at a mass concentration of 10% under the action of vigorous mechanical stirring at ambient temperature.

The clear solution is then filtered under a pressure of 0.2 MPa on a Millipore-type filter that has a cutoff threshold of 1 µm. This solution is then put in the form of a film using a 300 µm spiraled bar on a glass plate that was previously degreased with acetone and then dried.

The plate is inserted into a furnace. The evaporation of the solvent is carried out by a gradual elevation of the temperature up to 200° C. The final temperature is kept level for two hours. After cooling, the plate is immersed in water, where the separation of the film is observed.

After the solvent evaporates, the film that is obtained has a mean thickness of 24 µm.

The performance levels of the film that is obtained according to Example 4 for the propylene/propane separation have been obtained under test conditions that are identical to those that are described in Example 1.

TABLE 6

Performance Levels of the BTDA-BDAF Polyimide Membrane (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 Mixture | 0.8 MPa | 50° C. | 4 Barrers | 12 |
| 70/30 Mixture | 0.8 MPa | 50° C. | 3 Barrers | 12 |

Example 5

According to the Invention

The BPDA-BDAF polymer film that is the object of Example 5 is the result of the polycondensation of the 3,3',4,4'-bis-phenyltetracarboxylic acid dianhydride (BPDA) and the 9,9'-bis-(4-aminophenyl)fluorene (BDAF) in an equimolar mixture.

The monomers are introduced into the DMAC solvent under inert atmosphere and in an anhydrous medium.

After 8 hours of stirring at ambient temperature, the acid polyamide is obtained.

The second stage consists of a thermal dehydration of this acid polyamide in film form by heating (for one hour at 100° C., three hours at 200° C.) in a furnace.

After the solvent evaporates, the film that is obtained has a mean thickness of 40 µm.

The performance levels of the film that is obtained according to Example 5 for the propylene/propane separation have been obtained under test conditions that are identical to those described in Example 1.

Example 6

According to the Invention

The 6FDA-BDAF/TrMPD (50/50) polymer that is the object of Example 6 is the result of the polycondensation in an equimolar mixture of the hexafluoropropylidene-4,4'-diphthalic acid dianhydride (6FDA) and two diamines in a 50/50 molar proportion, the 9,9'-bis(4-aminophenyl)fluorene (BDAF) and the 2,4,6-trimethyl phenylenediamine (TrMPD).

After purification of the monomers by recrystallization in suitable solvents, the polycondensation of the polyimide is carried out in two stages: in a first step, the acid polyamide is produced at ambient temperature, and then the polyimide is obtained in a second cyclization stage by a chemical method.

During the first polymerization stage, the mixing of the dianhydride and diamines is carried out under inert atmosphere and in an anhydrous medium in the DMAC solvent.

The cyclo-dehydration stage is carried out by drop-by-drop addition of a cyclizing mixture that consists of triethylamine and acetic anhydride mixed in the synthesis solvent.

The thus obtained polyimide is then precipitated in water and then ground. The solid polymer is then filtered, rinsed, and then vacuum-dried in a furnace by gradually increasing the temperature until reaching 150° C. The inherent viscosity of the polymer that is thus obtained is 0.5 dl/g.

The material in ground form is then put into solution in the DMAC at a mass concentration of 12% under the action of vigorous mechanical stirring at ambient temperature.

The clear solution is then filtered under a pressure of 0.2 MPa on a Millipore-type filter that has a cutoff threshold of 1 µm. This solution is then put into the form of a film using a 300 µm spiraled bar on a glass plate that was previously degreased with acetone, and then dried.

The plate is inserted into a furnace. The evaporation of the solvent is carried out by a gradual elevation of the temperature up to 200° C. The final temperature is kept level for two hours. After cooling, the plate is immersed in water, where the separation of the film is observed. After the solvent evaporates, the film that is obtained has a mean thickness of 23 µm.

The sustained performance levels of the film that is obtained according to Example 6 for the propylene/propane separation have been measured under test conditions that are identical to those that are described in Example 1.

TABLE 7

Performance Levels of the BPDA-BDAF Polyimide Membrane (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 Mixture | 0.8 MPa | 50° C. | 2 Barrers | 20 |
| 70/30 Mixture | 0.8 MPa | 50° C. | 1.5 Barrers | 16 |

TABLE 8

Performance Levels of the 6FDA-BDAF/TrMPD (50/50)
Polyimide Membrane (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 | 0.8 MPa | 60° C. | 22 Barrers | 7 |
| 70/30 | 0.8 MPa | 60° C. | 20 Barrers | 7 |

Example No. 7

According to the Prior Art

The 6FDA-TrMPD-type polyimide was identified in the prior art as offering properties that are superior to all of the other polyimides evaluated in the prior art for the propylene/propane separation, because it has a propylene permeability that is greater than 1 barrer. In addition, this polymer offers a propylene/propane selectivity that is greater than 10 (ideal selectivity). These performance levels are summarized by Tables 9 and 10 below:

TABLE 9

Permeabilities of the 6FDA-TrMPD-Type Polyimide to Propylene and Propane Measured During Permeation Experiments in Pure Objects at 50° C. (Tanaka, K.; Taguchi, A.; Hao, J.; Kita, H.; Okamoto, K., Journal of Membrane Science, 121 (1996) 197-207).

| Pressure (Bar) | Propylene Permeability (Barrer) | Propane Permeability (Barrer) | $C_3H_6$ Permeability/ $C_3H_8$ Permeability (Ideal Selectivity) |
|---|---|---|---|
| 1 | 30 | 2.1 | 14.3 |
| 1.5 | 27 | 2 | 13.5 |
| 2 | 26 | 2 | 13.0 |
| 3 | 24 | 1.8 | 13.3 |
| 5 | 22 | 1.9 | 11.6 |
| 6 | 23 | 2 | 11.5 |
| 7 | 25** | 2.2 | 11.4 |

**Extrapolated Value

The degradation of the performance levels of the 6FDA-TrMPD-type polyimide with increasing pressures because of the plasticization mechanisms is still more pronounced during the separation tests of propylene/propane in a mixture that are conducted by Tanaka et al. 1996. Table 10 actually shows that the mixture selectivity of 6FDA-TrMPD is nearly two times lower than the ideal selectivity with regard to the propylene/propane mixture.

TABLE 10

Comparison of the Ideal Performance Levels and in a Mixture of the 6FDA-TrMPD-Type Polyimide for the Propylene/Propane Separation (Tanaka, K.; Taguchi, A.; Hao, J.; Kita, H.; Okamoto, K., Journal of Membrane Science, 121 (1996) 197-207).

| Composition of the Feedstock (% Propylene; % Propane) | Pressure Difference between the Upstream and Downstream Faces of the Film | Temperature of the Film | $C_3H_6$ Permeability (Barrer) | $C_3H_6$ Permeability/ $C_3H_8$ Permeability |
|---|---|---|---|---|
| Pure Compounds | 0.4 MPa | 50° C. | 27 Barrers | 10* |
| 50/50 Mixture | 0.4 MPa | 50° C. | 20 Barrers | 6** |
| Pure Compounds | 0.6 MPa | 50° C. | 25 Barrers | 9* |
| 50/50 Mixture | 0.6 MPa | 50° C. | 20 Barrers | 5** |

*Ideal Selectivity
**Mixture Selectivity

As Tables 9 and 10 above clearly show, the performance levels of the 6FDA-TrMPD polymer are lower than those of the polymers that are presented in Examples 1 to 6 according to this invention.

The claimed materials in this invention are actually:
Either more selective than the best polyimide of the prior art described in Table 9 (Examples 2 to 5) while offering permeability with regard to the propylene that is greater than 1 barren
Or more permeable (by a factor of 4) than the best polyimide of the prior art that is described in Table 9 (Example 1), while offering a propylene/propane selectivity in a comparable mixture under operating conditions that further promote the plasticization mechanisms.

Example 8

For Comparison

So as to confirm the increase offered by the 6FDA-BDAF-type polyimide relative to the 6FDA-TrMPD-type polyimide for the propylene/propane separation, it was selected to synthesize a 6FDA-TrMPD film so as to evaluate its performance levels under operating conditions that are similar to those that are described in Examples 1 to 6 according to the invention.

The synthesis of the 6FDA-TrMPD-type polymer was carried out in the following way:

After 2 hours at ambient temperature, the mixture of NMP, TrMPD diamine and dianhydride is brought to 100° C.

After 1 hour at 100° C., the mixture is brought in stages to 200° C. At this temperature, a gradual increase in the viscosity of the mixture is observed. The polymer is precipitated in water, washed, and then dried for 6 hours at 80° C. under vacuum. The inherent viscosity of the polymer in the NMP that is thus obtained is 0.54 dl/g.

The material is put into solution in the NMP at a mass concentration of 10% under the action of vigorous mechanical stirring at ambient temperature. The clear solution is then filtered under a pressure of 0.2 MPa on a Millipore-type filter that has a cutoff threshold of 1 μm.

This solution is then put into the form of a film using a 300 μm spiraled bar on a glass plate that was previously degreased with acetone, and then dried.

The plate is inserted into a furnace. The evaporation of the solvent is carried out by a gradual elevation of the temperature up to 200° C.

The final temperature is kept level for one hour. After cooling, the plate is immersed in water, where the separation of the film is observed. The film is then dried in a furnace at 50° C. for 24 hours.

After the solvent evaporates, the film that is obtained has a mean thickness of 35 μm.

The performance levels of the film that is obtained according to Example 8 for the propylene/propane separation have been obtained under test conditions that are identical to those that are described in Example No. 1

The performance levels that are obtained with the 6FDA-TrMPD-based film that is manufactured under the conditions described above are close to those of the 6FDA-TrMPD-based films that are described by Tanaka et al. 1996.

A sample of each membrane was tested in a circular permeation cell with an effective diameter of 5.5 cm placed in a thermostated chamber.

The upstream face of the thus tested membrane is flushed for 48 hours with a gas stream of 10 Nl/h that consists of ethylene and ethane, with a respective molar fraction of 90% and 10%, whereas the compartment downstream from the membrane, in which the permeate is collected, is flushed by a nitrogen stream of 1 Nl/h at atmospheric pressure.

The composition of the different fluids entering and exiting from the different compartments of the permeation cell is obtained by gas phase chromatography.

The performance levels of the membranes that are synthesized according to Examples 1, 2 and 3 are presented in detail in Table No. 13.

TABLE 11

Performance Levels of the 6FDA-TrMPD Polyimide (Load Pressure = 0.9 MPa)

| Composition of the Feedstock (% Propylene; % Propane) | Pressure Difference between the Upstream and Downstream Faces of the Film | Temperature of the Film | $C_3H_6$ Permeability (Barrer) | $C_3H_6$ Permeability/ $C_3H_8$ Permeability (Mixture Selectivity) |
|---|---|---|---|---|
| 90/10 | 0.8 MPa | 50° C. | 15 Barrers | 6 |
| 70/30 | 0.8 MPa | 50° C. | 16 Barrers | 6 |

TABLE 12

Performance Levels of the 6FDA-TrMPD Polyimide (Load Pressure = 1.7 MPa)

| Composition of the Feedstock (% Propylene; % Propane) | Pressure Difference between the Upstream and Downstream Faces of the Film | Temperature of the Film | $C_3H_6$ Permeability | $C_3H_6$ Permeability/ $C_3H_8$ Permeability (Mixture Selectivity) |
|---|---|---|---|---|
| 90/10 Mixture | 0.8 MPa | 60° C. | 17 Barrers | 5 |
| 70/30 Mixture | 0.8 MPa | 60° C. | 18 Barrers | 4.5 |

Example 9

According to the Invention

The membranes that were synthesized according to Examples 1 to 3 according to the invention have also been tested for separating ethylene from ethane.

TABLE 13

Performance Levels of the 6FDA-BDAF Polyimide
(Load Pressure = 0.9 MPa; Mixture to Be Separated that Consists of
90 mol % of Ethylene and 10 mol % of Ethane)

| Membrane Model | Pressure Difference between the Upstream and Downstream Faces of the Film | Temperature of the Film | $C_2H_6$ Permeability (Barrer) | $C_2H_6$ Permeability/ $C_2H_8$ Permeability (Mixture Selectivity) |
|---|---|---|---|---|
| Synthesized According to | 0.8 MPa | 60° C. | 3 | 3.1 |

TABLE 13-continued

Performance Levels of the 6FDA-BDAF Polyimide
(Load Pressure = 0.9 MPa; Mixture to Be Separated that Consists of
90 mol % of Ethylene and 10 mol % of Ethane)

| Membrane Model | Pressure Difference between the Upstream and Downstream Faces of the Film | Temperature of the Film | $C_2H_6$ Permeability (Barrer) | $C_2H_6$ Permeability/ $C_2H_8$ Permeability (Mixture Selectivity) |
|---|---|---|---|---|
| the Method Presented in Detail in Example No. 1 Synthesized According to the Method Presented in Detail in Example No. 2 | 0.8 MPa | 60° C. | 2.6 | 3.4 |
| Synthesized According to the Method Presented in Detail in Example No. 3 | 0.8 MPa | 60° C. | 2.3 | 4.2 |

It clearly appears that the films that are described according to Example Nos. 1 to 3 offer a significant ethylene/ethane selectivity while retaining a high permeability in relation to the ethylene, greater than 1 barrer. Clearly, the post heat treatment of this type of membrane leads to an increase in selectivity of the membrane.

Example 10

According to the Invention

A composite membrane that offers an olefin/paraffin selectivity that uses a selective layer according to the method that is described in this invention was synthesized by coating hollow fibers with phenylene polyoxide (PPO) that is produced by the Parker Filtration Company (Parker Hannifin SA, UCC France, Rue Albert Calmette, P. O. Box 6, 41260 La Chaussée St. Victor, France) according to the following method:

The 6FDA-BDAF-type polymer that is obtained according to Method No. 2 is put into solution in the DMAC at a mass concentration of 8% under the action of vigorous mechanical stirring at ambient temperature. The clear solution is then filtered under a pressure of 0.2 MPa on a Millipore-type filter that has a cutoff threshold of 1 µm. The poly-2,6-dimethyl-1, 4-phenylene oxide fiber is quenched in the diluted polymer solution, and then it is extracted vertically from the solution by taking care that excess solution is evacuated by gravity.

The coated fiber is then put out to dry vertically in a study under an inert atmosphere according to the following heating program: 30 minutes at 100° C., 2 hours at 160° C.

Samples of coated fibers analyzed by scanning electronic microscopy showed that the selective polyimide layer in olefins had a thickness of between 0.1 and 0.5 µm.

A fiber bundle is then set in a calender with the epoxy resin and is subjected to tests for separation of the propylene/propane mixture in the gaseous state under the conditions that are described in Example No. 1. During the tests for separation of mixtures that consist of propylene and propane at respective molar ratios of 90% and 10%, at a temperature of 50° C., and pressures upstream and downstream from the membrane respectively of 0.9 and 0.1 MPa, the mixture selectivity of the composite fibers is 6.5.

The invention claimed is:

1. A process for membrane separation of hydrocarbons, comprising selective separation of an olefin that is ethylene or propylene from an alkane of corresponding carbon number as that of the olefin that is to be separated, by subjecting the olefin and alkane to a membrane having a selective layer comprising a dense polymer film that is a polyimide obtained from polycondensation of 2,2-bis(3,4-dicarboxyphenyl)-hexafluoropropanoic acid dianhydride and 9,9-bis(4-aminophenyl)fluorene diamine;
   a polyimide obtained from polycondensation of 3,3',4,4'-biphenyltetracarboxylic acid dianhydride and 9,9-bis(4-aminophenyl)fluorene diamine;
   a polyimide obtained from polycondensation of 3,3',4,4'-benzophenone-tetracarboxylic acid dianhydride and 9,9-bis(4-aminophenyl)fluorene diamine;
   a polyimide obtained from polycondensation of (1) a 2,2-bis(3,4-dicarboxyphenyl)-hexafluoropropanoic acid dianhydride and (2) a mixture of 9,9-bis(4-aminophenyl)fluorene diamine and 1,3-diamino-2,4,6-trimethylbenzene diamine;
   a polyimide obtained from polycondensation of (1) 3,3',4,4'-biphenyltetracarboxylic acid dianhydride and (2) a mixture of 9,9-bis(4-aminophenyl)fluorene diamine and 1,3-diamino-2,4,6-trimethylbenzene diamine, or
   a polyimide obtained from polycondensation of (1) 3,3',4,4'-benzophenonetetracarboxylic acid dianhydride and (2) a mixture of 9,9-bis(4-aminophenyl)fluorene diamine and 1,3-diamino-2,4,6-trimethylbenzene diamine.

2. The process according to claim 1, in which the olefin that is to be separated from the hydrocarbon mixture is ethylene.

3. The process according to claim 1, in which the olefin that is to be separated from the hydrocarbon mixture is propylene.

4. The process according to claim 1, having an olefin partial pressure during separation greater than 0.3 MPa.

5. The process according to claim 1, in which the film that comprises the selective layer of the polymer membrane has undergone a post heat treatment at a temperature of more than 250° C. for at least one hour, designed to increase the selectivity of the polymer film.

6. The process according to claim 1, in which the selective layer is deposited on the surface of a hollow-fiber-type substrate comprising poly-2,6-dimethyl-1,4-phenylene oxide.

7. The process for membrane separation according to claim 1, in which the temperature of the process is between −60° C. and 100° C., and the pressure of the mixture that is to be separated is between 0.1 and 5 MPa.

8. The process for membrane separation according to claim 1, in which the temperature of the process is between 30° C. and 80° C., and the pressure of the mixture that is to be separated is between 1 and 3 MPa.

9. A process for membrane separation of hydrocarbons, comprising selective separation of an olefin that is ethylene or propylene from an alkane of corresponding carbon number as that of the olefin that is to be separated, by subjecting the olefin and alkane to a membrane having a selective layer comprising a dense polymer film that is a polyimide obtained from polycondensation of 2,2-bis(3,4-dicarboxyphenyl)-hexafluoropropanoic acid dianhydride and 9,9-bis(4-aminophenyl)fluorene diamine;

a polyimide obtained from polycondensation of 3,3',4,4'-biphenyltetracarboxylic acid dianhydride and 9,9-bis(4-aminophenyl)fluorene diamine;

a polyimide obtained from polycondensation of 3,3',4,4'-benzophenone-tetracarboxylic acid dianhydride and 9,9-bis(4-aminophenyl)fluorene diamine;

a polyimide obtained from polycondensation of (1) a 2,2-bis(3,4-dicarboxyphenyl)-hexafluoropropanoic acid dianhydride and (2) a mixture of 9,9-bis(4-aminophenyl)fluorene diamine and 1,3-diamino-2,4,6-trimethylbenzene diamine;

a polyimide obtained from polycondensation of (1) 3,3',4,4'-biphenyltetracarboxylic acid dianhydride and (2) a mixture of 9,9-bis(4-aminophenyl)fluorene diamine and 1,3-diamino-2,4,6-trimethylbenzene diamine, or a polyimide obtained from polycondensation of (1) 3,3',4,4'-benzophenonetetracarboxylic acid dianhydride and (2) a mixture of 9,9-bis(4-aminophenyl)fluorene diamine and 1,3-diamino-2,4,6-trimethylbenzene diamine in which the temperature of the process is between 40° C. and 70° C., and the pressure of the mixture that is to be separated is between 1 and 2 MPa.

* * * * *